US012590221B2

(12) United States Patent
Namgung et al.

(10) Patent No.: US 12,590,221 B2
(45) Date of Patent: Mar. 31, 2026

(54) RESIST TOPCOAT COMPOSITION, AND METHOD OF FORMING PATTERNS USING THE COMPOSITION

(71) Applicants: SAMSUNG SDI CO., LTD., Yongin-si (KR); SAMSUNG ELECTRONICS CO., LTD., Suwon-si (KR)

(72) Inventors: Ran Namgung, Suwon-si (KR); Hyeon Park, Suwon-si (KR); Shinhyo Bae, Suwon-si (KR); Daeseok Song, Suwon-si (KR); Minki Chon, Suwon-si (KR); Jun Soo Kim, Hwaseong-si (KR); Hyun-Woo Kim, Seongnam-si (KR); Hyun-Ji Song, Anyang-si (KR); Young Joo Choi, Hwaseong-si (KR); Suk-Koo Hong, Hwaseong-si (KR)

(73) Assignees: Samsung SDI Co., Ltd., Yongin-si (KR); Samsung Electronics Co., Ltd., Yongin-si (KR)

( * ) Notice: Subject to any disclaimer, the term of this patent is extended or adjusted under 35 U.S.C. 154(b) by 787 days.

(21) Appl. No.: 17/742,260

(22) Filed: May 11, 2022

(65) Prior Publication Data

US 2023/0021469 A1 Jan. 26, 2023

(30) Foreign Application Priority Data

Jul. 1, 2021 (KR) ........................ 10-2021-0086513

(51) Int. Cl.
*C09D 167/04* (2006.01)
*C07C 31/38* (2006.01)
(Continued)

(52) U.S. Cl.
CPC ............ *C09D 167/04* (2013.01); *C07C 31/38* (2013.01); *C07C 37/02* (2013.01); *C07C 323/03* (2013.01);
(Continued)

(58) Field of Classification Search
CPC .... C09D 167/04; C09D 133/16; C07C 31/38; C07C 37/02; C07C 323/03; C07C 53/21;
(Continued)

(56) References Cited

U.S. PATENT DOCUMENTS 6,764,806 B2 7/2004 Jung et al.
7,214,467 B2 5/2007 Kanna et al.
(Continued)

FOREIGN PATENT DOCUMENTS

CN 103186038 A 7/2013
CN 103258720 A 8/2013
(Continued)

OTHER PUBLICATIONS

Korean Office Action dated Jul. 29, 2024, of the corresponding Korean Patent Application No. 10-2021-0086513 (7 pages).
(Continued)

*Primary Examiner* — Caleen O Sullivan
(74) *Attorney, Agent, or Firm* — Womble Bond Dickinson (US) LLP

(57) ABSTRACT

A resist topcoat composition and a method of forming patterns using the resist topcoat composition. The resist topcoat composition includes an acrylic copolymer including a first structural unit represented by Chemical Formula M-1, and a second structural unit represented by Chemical Formula M-2; an acid compound; and a solvent Chemical Formula M-1

(Continued)

-continued

Chemical Formula M-2

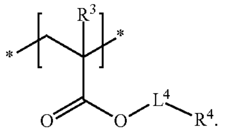

19 Claims, 1 Drawing Sheet

(51) Int. Cl.

| | |
|---|---|
| ***C07C 37/02*** | (2006.01) |
| ***C07C 323/03*** | (2006.01) |
| ***C07D 285/15*** | (2006.01) |
| ***C08G 63/47*** | (2006.01) |
| ***C08G 63/682*** | (2006.01) |
| ***G03F 7/004*** | (2006.01) |
| ***G03F 7/16*** | (2006.01) |

(52) U.S. Cl.

CPC ........... *C07D 285/15* (2013.01); *C08G 63/47* (2013.01); *C08G 63/6822* (2013.01); *G03F 7/0041* (2013.01); *G03F 7/168* (2013.01)

(58) Field of Classification Search

CPC ..... C07C 63/70; C07C 309/06; C07C 311/48; C07D 285/15; C08G 63/47; C08G 63/6822; G03F 7/0041; G03F 7/168; G03F 7/405; G03F 7/40; G03F 7/42; G03F 7/426; C08F 220/24; C08F 220/282; C08F 2/44; C08F 220/18; C08F 220/22; C08F 220/1808; C08F 220/286; C08L 33/16; C08K 5/095; C08K 5/42; C08K 5/43; C08K 5/46; H01L 21/3088

USPC ............. 430/311, 270.1, 271.1, 272.1, 273.1

See application file for complete search history.

(56) References Cited

U.S. PATENT DOCUMENTS

| | | | | |
|---|---|---|---|---|
| 2005/0284502 | A1 | 12/2005 | Watanabe et al. | |
| 2006/0111550 | A1 | 5/2006 | Hata et al. | |
| 2006/0127803 | A1 | 6/2006 | Jung et al. | |
| 2006/0275697 | A1 | 12/2006 | Hata et al. | |
| 2007/0031755 | A1 | 2/2007 | Hirayama et al. | |
| 2007/0087125 | A1 | 4/2007 | Maeda et al. | |
| 2007/0178407 | A1 | 8/2007 | Hatakeyama et al. | |
| 2010/0003615 | A1 | 1/2010 | Nakamura et al. | |
| 2010/0104978 | A1 | 4/2010 | Sawano et al. | |
| 2010/0266953 | A1* | 10/2010 | Chiba ....................... | G03F 7/11 430/270.1 |
| 2011/0123933 | A1 | 5/2011 | Yun et al. | |
| 2013/0244438 | A1 | 9/2013 | Bae et al. | |
| 2015/0004544 | A1 | 1/2015 | Namai | |
| 2015/0086929 | A1 | 3/2015 | Hatakeyama et al. | |
| 2015/0185620 | A1 | 7/2015 | Liu et al. | |
| 2016/0097979 | A1 | 4/2016 | Tsunoda et al. | |
| 2016/0202612 | A1 | 7/2016 | Hatakeyama et al. | |
| 2017/0170008 | A1 | 6/2017 | Park et al. | |
| 2017/0255102 | A1 | 9/2017 | Rowell et al. | |
| 2017/0255103 | A1 | 9/2017 | Rowell et al. | |
| 2017/0293227 | A1 | 10/2017 | Nishita et al. | |
| 2018/0188654 | A1 | 7/2018 | Rowell et al. | |
| 2019/0146342 | A1 | 5/2019 | Zi et al. | |
| 2019/0243246 | A1 | 8/2019 | Kaur et al. | |
| 2020/0192220 | A1 | 6/2020 | Yagi et al. | |
| 2020/0319551 | A1 | 10/2020 | Tsuchimura et al. | |
| 2020/0379353 | A1 | 12/2020 | Kaur et al. | |
| 2021/0055653 | A1 | 2/2021 | Yoshimura et al. | |
| 2023/0021469 | A1 | 1/2023 | Namgung et al. | |
| 2023/0024422 | A1 | 1/2023 | Namgung et al. | |
| 2023/0026721 | A1 | 1/2023 | Namgung et al. | |
| 2023/0028244 | A1 | 1/2023 | Namgung et al. | |
| 2023/0032354 | A1 | 2/2023 | Namgung et al. | |

FOREIGN PATENT DOCUMENTS

| | | | |
|---|---|---|---|
| CN | 104749888 | A | 7/2015 |
| JP | 9-291228 | A | 11/1997 |
| JP | 2005-157259 | A | 6/2005 |
| JP | 2006-23699 | A | 1/2006 |
| JP | 2006-58404 | A | 3/2006 |
| JP | 2008-286924 | A | 11/2008 |
| JP | 2009-145658 | A | 7/2009 |
| JP | 2010-275498 | A | 12/2010 |
| JP | 2011-17921 | A | 1/2011 |
| JP | 2012-68628 | A | 4/2012 |
| JP | 2013-218191 | A | 10/2013 |
| JP | 5381298 | B2 | 1/2014 |
| JP | 5617810 | B2 | 11/2014 |
| JP | 6525389 | B2 | 6/2019 |
| JP | 6818731 | B2 | 1/2021 |
| JP | 6823992 | B2 | 2/2021 |
| KR | 10-2001-0089151 | A | 9/2001 |
| KR | 10-0574496 | B1 | 4/2006 |
| KR | 10-2006-0049679 | A | 5/2006 |
| KR | 10-0574993 | B1 | 5/2006 |
| KR | 10-2006-0064054 | A | 6/2006 |
| KR | 10-0640643 | B1 | 10/2006 |
| KR | 10-2007-0041287 | A | 4/2007 |
| KR | 10-2008-0099913 | A | 11/2008 |
| KR | 10-2009-0106562 | A | 10/2009 |
| KR | 10-0926021 | B1 | 11/2009 |
| KR | 10-0962951 | B1 | 6/2010 |
| KR | 10-2010-0098024 | A | 9/2010 |
| KR | 10-2011-0009005 | A | 1/2011 |
| KR | 10-2011-0056153 | A | 5/2011 |
| KR | 10-1112599 | B1 | 2/2012 |
| KR | 10-2012-0111532 | A | 10/2012 |
| KR | 10-1384811 | B1 | 4/2014 |
| KR | 10-1428121 | B1 | 8/2014 |
| KR | 10-2014-0120212 | A | 10/2014 |
| KR | 10-1486843 | B1 | 1/2015 |
| KR | 10-2015-0080434 | A | 7/2015 |
| KR | 10-2017-0007185 | A | 1/2017 |
| KR | 10-1807198 | B1 | 12/2017 |
| KR | 10-1910832 | B1 | 10/2018 |
| KR | 10-1940003 | B1 | 1/2019 |
| KR | 10-2029693 | B1 | 10/2019 |
| KR | 10-2069186 | B1 | 1/2020 |
| KR | 10-2100432 | B1 | 5/2020 |
| KR | 10-2020-0138007 | A | 12/2020 |
| KR | 10-2195470 | B1 | 12/2020 |
| KR | 10-2203366 | B1 | 1/2021 |
| WO | 2008/035640 | A1 | 3/2008 |
| WO | WO 2012/064097 | A2 | 5/2012 |
| WO | 2019/054311 | A1 | 3/2019 |
| WO | 2019/026549 | A1 | 7/2019 |

OTHER PUBLICATIONS

Korean Office Action dated Mar. 29, 2024, of the corresponding Korean Patent Application No. 10-2021-0086511 (7 pages).

Korean Office Action issued in corresponding KR Application No. 10-2021-0086512, dated Mar. 29, 2024, 7 pages.

Korean Office Action dated Aug. 1, 2024, of the corresponding Korean Patent Application No. 10-2021-0086530 (5 pages).

U.S. Office Action dated Oct. 7, 2024, issued in U.S. Appl. No. 17/749,899 (9 pages).

U.S. Office Action dated Dec. 4, 2024, issued in U.S. Appl. No. 17/734,772 (21 pages).

U.S. Office Action dated Jan. 29, 2025, issued in U.S. Appl. No. 17/733,743 (37 pages).

U.S. Office Action dated Feb. 7, 2025, issued in U.S. Appl. No. 17/847,794 (16 pages).

(56) References Cited

OTHER PUBLICATIONS

U.S. Office Action dated Mar. 13, 2025, issued in U.S. Appl. No. 17/746,811 (20 pages).
U.S. Final Office Action dated May 19, 2025, issued in U.S. Appl. No. 17/733,743 (32 pages).
U.S. Notice of Allowance dated Jun. 9, 2025, issued in U.S. Appl. No. 17/734,772 (10 pages).
U.S. Notice of Allowance dated Jul. 29, 2025, issued in U.S. Appl. No. 17/733,743 (8 pages).
U.S. Final Office Action dated Aug. 22, 2025, issued in U.S. Appl. No. 17/847,794 (23 pages).
U.S. Final Office Action dated Sep. 17, 2025, issued in U.S. Appl. No. 17/746,811 (18 pages).
U.S. Notice of Allowance dated Oct. 16, 2025, issued in U.S. Appl. No. 17/734,772 (11 pages).

* cited by examiner

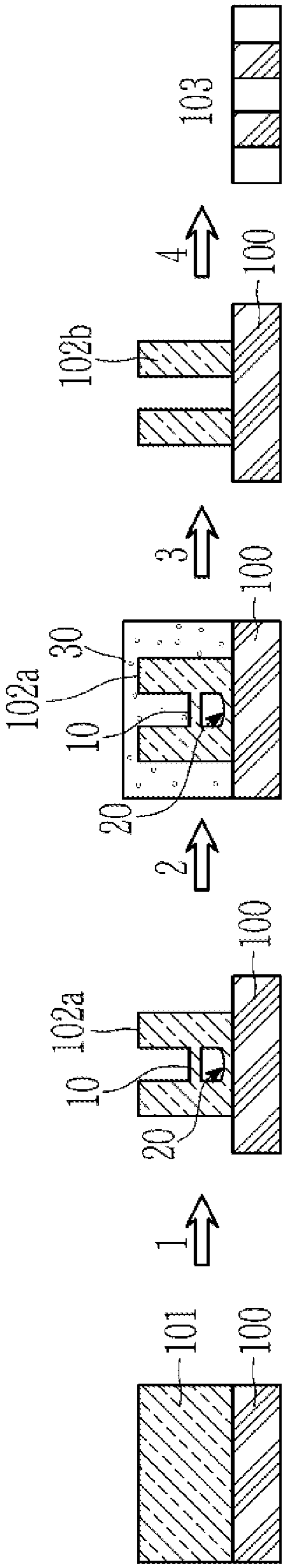
101
100
1
102a
10
20
100
2
102a
30
10
20
100
3
102b
100
4
103

RESIST TOPCOAT COMPOSITION, AND METHOD OF FORMING PATTERNS USING THE COMPOSITION

CROSS-REFERENCE TO RELATED APPLICATION

This application claims priority to and the benefit of Korean Patent Application No. 10-2021-0086513, filed in the Korean Intellectual Property Office on Jul. 1, 2021, the entire content of which is incorporated herein by reference.

BACKGROUND

1. Field

One or more aspects of embodiments of the present disclosure relate to a resist topcoat composition, and a method of forming patterns utilizing the same.

2. Description of the Related Art

Recently, the semiconductor industry has developed to the point of using ultrafine techniques providing patterns of several to several tens of nanometers in size (e.g., in nanometer scale). Such ultrafine techniques need effective lithographic techniques.

A lithographic technique in the art involves forming a material layer on a semiconductor substrate, coating a photoresist layer thereon, exposing and developing the photoresist layer to form a photoresist pattern, and then etching the material layer using the photoresist pattern as a mask.

As lithographic techniques are developed, a degree of pattern integration is increasing, and materials and technologies for solving various problems occurring in this process are desired. In particular, when a photoresist is patterned using extreme ultraviolet (EUV) as a light source, a high-resolution pattern may be realized, but single line open (SLO) defects may randomly occur on the pattern due to photon shot noise. These SLO defects may lower yield, and improved technology solutions are desired.

SUMMARY

One or more aspects of embodiments of the present disclosure are directed toward a resist topcoat composition capable of not only realizing high-resolution patterns, but also removing single line open (SLO) defects to improve yield is provided.

One or more aspects of embodiments of the present disclosure are directed toward a method of forming patterns utilizing the resist topcoat composition.

One or more embodiments of the present disclosure provide a resist topcoat composition including an acrylic copolymer including a first structural unit represented by Chemical Formula M-1 and a second structural unit represented by Chemical Formula M-2; an acid compound; and a solvent.

Chemical Formula M-1

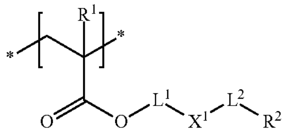

-continued

Chemical Formula M-2

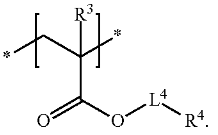

In Chemical Formula M-1 and Chemical Formula M-2, $R^1$ and $R^3$ may each independently be hydrogen or a substituted or unsubstituted C1 to C10 alkyl group, $R^2$ may be hydrogen, a fluorine, a hydroxy group, or a substituted or unsubstituted C1 to C20 alkyl group, $R^4$ may be a substituted or unsubstituted C1 to C20 alkyl group, or *—O-$L^3$-O—$R^5$, $L^1$ to $L^3$ may each independently be a single bond or a substituted or unsubstituted C1 to C10 alkylene group, $L^4$ may be a substituted or unsubstituted C5 to C20 alkylene group, $R^5$ may be a substituted or unsubstituted C1 to C10 alkyl group, $X^1$ may be a single bond, —O—, —S—, —S(O)—, —$S(O)_2$—, —C(O)—, —(CO)O—, —O(CO), —O(CO)O—, or —NR'— (wherein, R' is hydrogen, deuterium, or a C1 to C10 alkyl group), $R^2$, $L^1$, and $L^2$ together include a fluorine and a hydroxy group, and

* is a linking point.

The first structural unit may be represented by Chemical Formula 1:

Chemical Formula 1

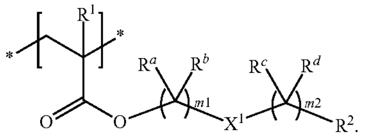

In Chemical Formula 1, $R^1$ may be hydrogen or a substituted or unsubstituted C1 to C10 alkyl group, $R^a$, $R^b$, $R^c$, $R^d$, and $R^2$ may each independently be hydrogen, a fluorine, a hydroxy group, or a substituted or unsubstituted C1 to C20 alkyl group, m1 and m2 may each independently be an integer from 1 to 10, $X^1$ may be a single bond, —O—, —S—, —S(O)—, —$S(O)_2$—, —C(O)—, —(CO)O—, —O(CO), —O(CO)O—, or —NR'— (wherein, R' is hydrogen, deuterium, or a C1 to C10 alkyl group), and $R^a$, $R^b$, $R^c$, $R^d$, and $R^2$ together include a fluorine and a hydroxy group.

In some embodiments, for example, $R^c$, $R^d$, and $R^2$ of Chemical Formula 1 together include fluorine and a hydroxy group.

For example, at least one of $R^c$ or $R^d$ in Chemical Formula 1 may be a fluorine or a C1 to C10 alkyl group substituted with at least one fluorine, and $R^2$ may be a hydroxy group or a C1 to C10 alkyl group substituted with at least one hydroxy group.

For example, at least one of $R^c$ or $R^d$ in Chemical Formula 1 may be a hydroxy group or a C1 to C10 alkyl group substituted with at least one hydroxy group, and $R^2$ may be a fluorine or a C1 to C10 alkyl group substituted with at least one fluorine.

For example, in Chemical Formula 1, $R^c$ may be a hydroxy group or a C1 to C10 alkyl group substituted with at least one hydroxy group, $R^d$ may be a fluorine or a C1 to C10 alkyl group substituted with at least one fluorine, and $R^2$ may be a hydroxy group, a fluorine, or a C1 to C10 alkyl group substituted with at least one fluorine or at least one hydroxy group.

For example, at least one of $R^c$ or $R^d$ of Chemical Formula 1 may be a fluorine or a C1 to C10 alkyl group substituted with at least one fluorine, and $R^2$ may be a hydroxy group, or a C1 to C10 alkyl group substituted with at least one hydroxy group and optionally at least one fluorine.

The first structural unit may be selected from Group I:

Group I

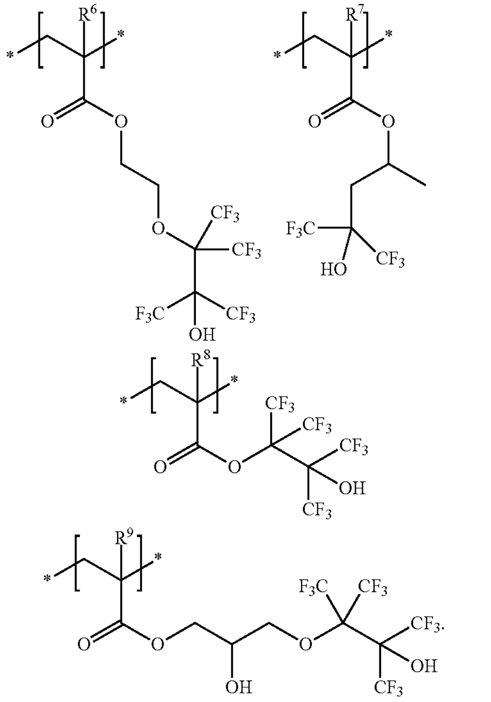

In Group I, $R^6$ to $R^9$ may each independently be hydrogen or a methyl group, and * is a linking point.

The second structural unit may be represented by Chemical Formula 2-1 or Chemical Formula 2-2:

Chemical Formula 2-1

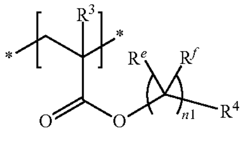

Chemical Formula 2-2

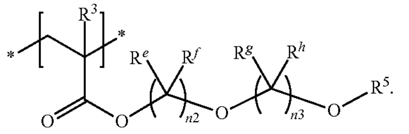

In Chemical Formula 2-1 and Chemical Formula 2-2, $R^3$ may be hydrogen or a substituted or unsubstituted C1 to C10 alkyl group, $R^e$, $R^f$, $R^g$, $R^h$, $R^4$, and $R^5$ may each independently be hydrogen, a hydroxy group, or a substituted or unsubstituted C1 to C10 alkyl group, n1 may be an integer of 5 to 10, n2 and n3 may each independently be an integer of 1 to 10, and

* is a linking point.

The second structural unit may be selected from Group II:

Group II

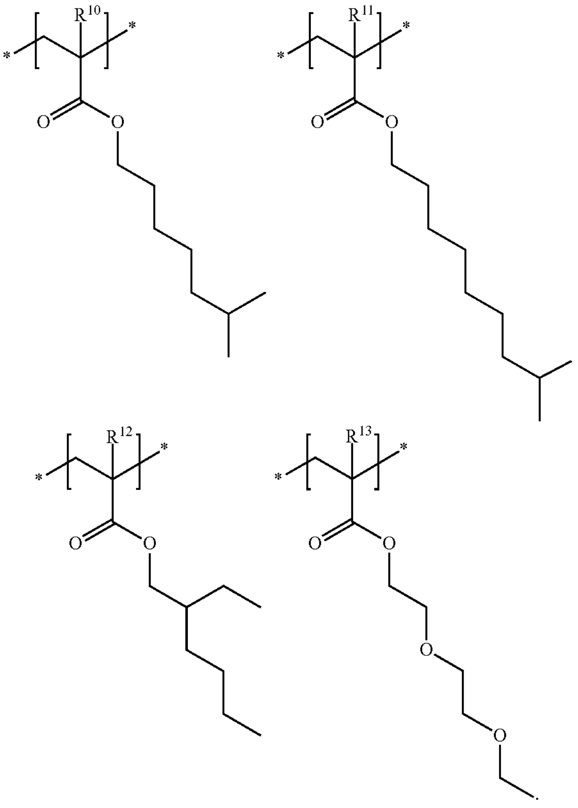

In Group II, $R^{10}$ to $R^{13}$ may each independently be hydrogen or a methyl group, and * is a linking point.

The acrylic copolymer may include the first structural unit and the second structural unit in a mole ratio of about 9:1 to about 5:5.

A weight average molecular weight of the acrylic copolymer may be about 1,000 g/mol to about 50,000 g/mol.

The acid compound may be at least one selected from a sulfonic acid compound containing at least one fluorine, a sulfonimide (e.g., disulfonimide) compound containing at least one fluorine, and a carboxylic acid compound containing at least one fluorine.

The acid compound may be represented by at least one of Chemical Formula 3 to Chemical Formula 6.

Chemical Formula 3

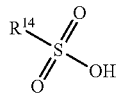

-continued

Chemical Formula 4

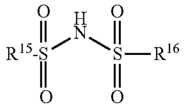

Chemical Formula 5

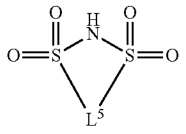

Chemical Formula 6

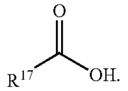

In Chemical Formula 3 to Chemical Formula 6, $R^{14}$ to $R^{17}$ may each independently be a fluorine, a C1 to C20 alkyl group substituted with at least one fluorine, a C2 to C20 alkenyl group substituted with at least one fluorine, a C2 to C20 alkynyl group substituted with at least one fluorine, a C3 to C20 cycloalkyl group substituted with at least one fluorine, a C3 to C20 cycloalkenyl group substituted with at least one fluorine, a C3 to C20 cycloalkynyl group substituted with at least one fluorine, a C6 to C20 aryl group substituted with at least one fluorine, or a C1 to C20 heteroaryl group substituted with at least one fluorine, and $L^5$ may be a C1 to C10 alkylene group substituted with at least one fluorine, a C3 to C20 cycloalkylene group substituted with at least one fluorine, a C6 to C20 arylene group substituted with at least one fluorine, or a C1 to C20 heteroarylene group substituted with at least one fluorine.

The acid compound may be selected from compounds of Group III.

Group III

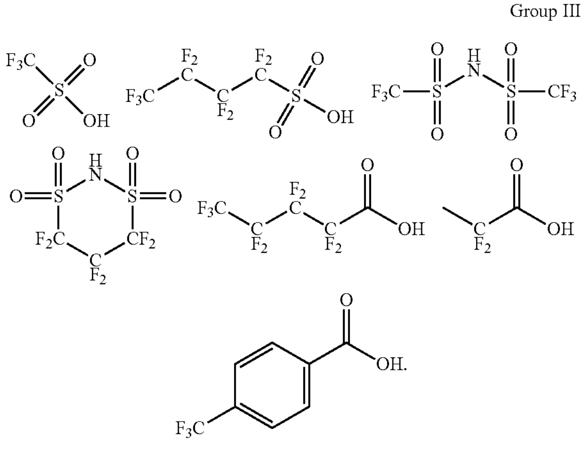

In the composition, the acrylic copolymer, and the acid compound may be included in a weight ratio of about 3:1 to about 30:1.

A total content (e.g., amount) of the acrylic copolymer and the acid compound may be about 0.1 wt % to about 10 wt % based on the total weight of the resist topcoat composition.

The composition may further include an additive including a surfactant, a thermal acid generator, a plasticizer, or a combination thereof.

The solvent may be an ether-based solvent represented by Chemical Formula 7:

Chemical Formula 7

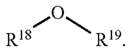

In Chemical Formula 7, $R^{18}$ and $R^{19}$ may each independently be a substituted or unsubstituted C3 to C20 alkyl group.

The ether-based solvent may be selected from diisopropyl ether, dipropyl ether, diisoamyl ether, diamyl ether, dibutyl ether, diisobutyl ether, di-sec-butyl ether, dihexyl ether, bis(2-ethylhexyl) ether, didecyl ether, diundecyl ether, didodecyl ether, ditetradecyl ether, hexadecyl ether, butyl methyl ether, butyl ethyl ether, butyl propyl ether, tert-butyl methyl ether, tert-butyl ethyl ether, tert-butylpropyl ether, di-tert-butyl ether, cyclopentylmethyl ether, cyclohexylmethyl ether, cyclopentylethyl ether, cyclohexylethyl ether, cyclopentylpropyl ether, cyclopentyl-2-propyl ether, cyclohexylpropyl ether, cyclohexyl-2-propyl ether, cyclopentylbutyl ether, cyclopentyl-tert-butyl ether, cyclohexylbutyl ether, cyclohexyl-tert-butyl ether, 2-octanone, 4-heptanone, and combinations thereof.

One or more embodiments of the present disclosure provide a method of forming patterns includes forming a photoresist pattern on a substrate, coating the aforementioned resist topcoat composition on the photoresist pattern, drying and heating the substrate on which the resist topcoat composition is coated to form a topcoat, and spraying a rinse solution on the substrate coated with the topcoat to remove the topcoat.

The heating of the substrate coated with the resist topcoat composition may be performed at a temperature of about 100° C. to about 500° C.

The resist topcoat composition according to an embodiment may have excellent or suitable solubility in a solvent having low reactivity with respect to the photoresist, and thus may effectively remove SLO defects without loss of photoresist fine patterns.

Because the aforementioned SLO defects may be removed by a simple process, it is advantageous in terms of process economy. Accordingly, the resist topcoat composition according to an embodiment or a pattern prepared therefrom may be advantageously utilized to form a fine pattern of a photoresist utilizing a high energy light source such as EUV.

BRIEF DESCRIPTION OF THE DRAWINGS

The drawing is a cross-sectional view for explaining a method of forming patterns utilizing a resist topcoat composition according to an embodiment.

DETAILED DESCRIPTION

Example embodiments of the present disclosure will hereinafter be described in more detail, and may be easily performed by a person skilled in the art. However, this disclosure may be embodied in many different forms and should not be construed as limited to the example embodiments set forth herein.

In the drawings, the thickness of layers, films, panels, regions, etc., may be exaggerated for clarity, and like reference numerals designate like elements throughout the specification. It will be understood that when an element such as a layer, film, region, or substrate is referred to as being "on" another element, it can be directly on the other element, or intervening elements may also be present. In contrast, when an element is referred to as being "directly on" another element, there are no intervening elements present.

As used herein, when a definition is not otherwise provided, "substituted" refers to replacement of a hydrogen atom (e.g., in a compound, group, or moiety) by a non-hydrogen atom substituent selected from a halogen atom (F, Br, Cl, and/or I), a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a vinyl group, a C1 to C20 alkyl group, a C2 to C20 alkenyl group, a C2 to C20 alkynyl group, a C6 to C30 aryl group, a C7 to C30 arylalkyl group, a C6 to C30 allyl group, a C1 to C30 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and combinations thereof.

As used herein, when a definition is not otherwise provided, "hetero" refers to the inclusion of 1 to 10 heteroatoms selected from nitrogen (N), oxygen (O), sulfur (S), and phosphorus (P).

In some embodiments, in the present specification, the term "acrylic polymer" refers to an acrylic polymer and a methacrylic polymer.

Unless otherwise specified in the present specification, the weight average molecular weight may be measured by dissolving a powder sample in tetrahydrofuran (THF) and then utilizing an Agilent 1200 series Gel Permeation Chromatography (GPC) (column is Shodex Company LF-804, standard sample is Shodex company polystyrene).

Unless otherwise defined in the specification, "*" indicates a linking point of a structural unit or a compound moiety of a compound.

As used herein, singular forms such as "a," "an," and "the" are intended to include the plural forms as well, unless the context clearly indicates otherwise. It will be further understood that the terms "includes," "including," "comprises," and/or "comprising," when used in this specification, specify the presence of stated features, steps, operations, elements, and/or components, but do not preclude the presence or addition of one or more other features, steps, operations, elements, components, and/or groups thereof.

As used herein, the terms "use," "using," and "used" may be considered synonymous with the terms "utilize," "utilizing," and "utilized," respectively. As used herein, expressions such as "at least one of," "one of," and "selected from," when preceding a list of elements, modify the entire list of elements and do not modify the individual elements of the list. As used herein, the term "and/or" includes any and all combinations of one or more of the associated listed items.

The term "may" will be understood to refer to "one or more embodiments," some of which include the described element and some of which exclude that element and/or include an alternate element. Similarly, alternative language such as "or" refers to "one or more embodiments," each including a corresponding listed item.

Hereinafter, a resist topcoat composition according to an embodiment is described.

One or more embodiments of the present disclosure relate to a resist topcoat composition capable of improving photoresist patterning (e.g., having improved photoresist patterning) by adding a simple process during the fine pattern forming process of photolithography utilizing a short-wavelength light source (such as an ArF excimer laser (wavelength: 193 nm)) or high energy rays (such as extreme ultraviolet (EUV; wavelength: 13.5 nm)) to remove or reduce SLO defects in the resist pattern, and a method for forming a photoresist pattern utilizing such a topcoat.

The resist topcoat composition according to an embodiment includes an acrylic copolymer including a first structural unit represented by Chemical Formula M-1, and a second structural unit represented by Chemical Formula M-2; an acid compound; and a solvent:

Chemical Formula M-1

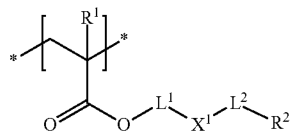

Chemical Formula M-2

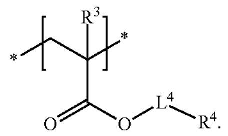

In Chemical Formula M-1 and Chemical Formula M-2, $R^1$ and $R^3$ may each independently be hydrogen or a substituted or unsubstituted C1 to C10 alkyl group, $R^2$ may be hydrogen, a fluorine, a hydroxy group, or a substituted or unsubstituted C1 to C20 alkyl group, $R^4$ may be a substituted or unsubstituted C1 to C20 alkyl group, or $*—O-L^3-O—R^5$, $L^1$ to $L^3$ may each independently be a single bond or a substituted or unsubstituted C1 to C10 alkylene group, $L^4$ may be a substituted or unsubstituted C5 to C20 alkylene group, $R^5$ may be a substituted or unsubstituted C1 to C10 alkyl group, $X^1$ may be a single bond, —O—, —S—, —S(O)—, $—S(O)_2—$, —C(O)—, —(CO)O—, —O(CO), —O(CO)O—, or —NR'— (wherein, R' is hydrogen, deuterium, or a C1 to C10 alkyl group), $R^2$, $L^1$, and $L^2$ include (e.g., together include) a fluorine and a hydroxy group, and

* is a linking point.

The composition according to embodiments is coated on the photoresist, and has excellent or suitable solubility in a solvent having low reactivity to the photoresist, so that it may be easily removed together with SLO defects, which is advantageous for realizing high resolution.

The formation and removal of the resist topcoat may be performed by relatively simple processes that are advantageous in terms of process economy, and the yield may be improved according to the removal of the SLO defects.

Because the acrylic copolymer included in the composition includes the first structural unit and the second structural unit at the same time, it has excellent or suitable solubility in an organic solvent, may be substantially uniformly coated on a pattern, and may minimize or reduce influence on the resist.

The statement that "$R^2$, $L^1$, and $L^2$ include a fluorine and a hydroxy group" indicates that at least one fluorine and at least one hydroxy group are included within the combination of $R^2$, $L^1$, and $L^2$, for example:

$R^2$ may be a C1 to C10 alkyl group substituted with at least one fluorine and at least one hydroxy group, or at least one of $L^1$ or $L^2$ may be a C1 to C10 alkylene group substituted with at least one fluorine and at least one hydroxy group, or at least one of $L^1$ or $L^2$ may be a C1 to C10 alkylene group substituted with at least one fluorine and the other may be a C1 to C10 allylene group substituted with at least one hydroxy group, or $R^2$ may be a fluorine and at least one of $L^1$ or $L^2$ may be a C1 to C10 alkylene group substituted with a hydroxy group, or $R^2$ may be a hydroxy group and at least one of $L^1$ or $L^2$ may be a C1 to C10 alkylene group substituted with a fluorine, or $R^2$ may be a C1 to C10 alkyl group substituted with at least one fluorine and at least one hydroxy group, or $R^2$ may be a C1 to C10 alkyl group substituted with a C1 to C10 alkyl group substituted with at least one hydroxy group and at least one fluorine.

For example, the first structural unit may be represented by Chemical Formula 1:

Chemical Formula 1

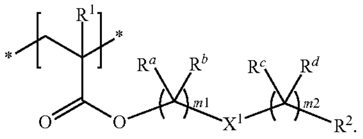

In Chemical Formula 1, $R^1$ may be hydrogen or a substituted or unsubstituted C1 to C10 alkyl group, $R^a$, $R^b$, $R^c$, $R^d$, and $R^2$ may each independently be hydrogen, a fluorine, a hydroxy group, or a substituted or unsubstituted C1 to C20 alkyl group, m1 and m2 may each independently be an integer from 1 to 10, $X^1$ may be a single bond, —O—, —S—, —S(O)—, —$S(O)_2$—, —C(O)—, —(CO)O—, —O(CO), —O(CO)O—, —NR'— (wherein R' is hydrogen, deuterium, or a C1 to C10 alkyl group), and $R^a$, $R^b$, $R^c$, $R^d$, and $R^2$ include (e.g., together include) a fluorine and a hydroxy group.

The statement that "$R^a$, $R^b$, $R^c$, $R^d$, and $R^2$ (together) include a fluorine and a hydroxy group" indicates that at least one fluorine and at least one hydroxy group are included within the combination of $R^a$, $R^b$, $R^c$, $R^d$, and $R^2$, for example:

at least one of $R^a$, $R^b$, $R^c$, $R^d$, or $R^2$ may each independently be a C1 to C10 alkyl group substituted with a fluorine, and at least one of the remaining groups may each independently be a C1 to C10 alkyl group substituted with a hydroxy group, or at least one of $R^a$, $R^b$, $R^c$, $R^d$, or $R^2$ may each independently be a C1 to C10 alkyl group substituted with a hydroxy group and a fluorine, or at least one of $R^a$, $R^b$, $R^c$, $R^d$, or $R^2$ may each independently be a C1 to C10 alkyl group substituted with a C1 to C10 alkyl group substituted with a hydroxy group and a fluorine, or at least one of $R^a$, $R^b$, $R^c$, $R^d$, or $R^2$ may be a fluorine and at least one of the remaining groups may be a hydroxy group, or at least one of $R^a$, $R^b$, $R^c$, $R^d$, or $R^2$ may be a fluorine and at least one of the remaining groups may be a C1 to C10 alkyl group substituted with a hydroxy group, or at least one of $R^a$, $R^b$, $R^c$, $R^d$, or $R^2$ may be a hydroxy group and at least one of the remaining groups may be a C1 to C10 alkyl group substituted with a fluorine, or at least one of $R^a$, $R^b$, $R^c$, $R^d$, or $R^2$ may be a C1 to C20 alkyl group substituted with a fluorine and at least one of the remaining groups may be a C1 to C20 alkyl group substituted with a hydroxy group.

For example, $R^1$ may be hydrogen or a methyl group, $X^1$ may be a single bond or —O—, and $R^2$ may be a fluorine, a hydroxy group, a C1 to C10 alkyl group substituted with at least one fluorine, or a C1 to C10 alkyl group substituted with at least one hydroxy group.

For example, $R^c$, $R^d$, and $R^2$ of Chemical Formula 1 may together include a fluorine and a hydroxy group.

For example, at least one of $R^c$ or $R^d$ in Chemical Formula 1 may be a fluorine or a C1 to C10 alkyl group substituted with at least one fluorine, and $R^2$ may be a hydroxy group or a C1 to C10 alkyl group substituted with at least one hydroxy group.

For example, at least one of $R^c$ or $R^d$ in Chemical Formula 1 may be a hydroxy group or a C1 to C10 alkyl group substituted with at least one hydroxy group, and $R^2$ may be a fluorine or a C1 to C10 alkyl group substituted with at least one fluorine.

For example, in Chemical Formula 1, $R^c$ may be a hydroxy group or a C1 to C10 alkyl group substituted with at least one hydroxy group, $R^d$ may be a fluorine or a C1 to C10 alkyl group substituted with at least one fluorine, and $R^2$ may be a hydroxy group, a fluorine, or a C1 to C10 alkyl group substituted with at least one fluorine and/or at least one hydroxy group.

For example, at least one of $R^c$ or $R^d$ of Chemical Formula 1 may be a fluorine or a C1 to C10 alkyl group substituted with at least one fluorine, and $R^2$ may be a hydroxy group or a C1 to C10 alkyl group substituted with at least one hydroxy group and/or at least one fluorine.

For example, the first structural unit may be selected from Group I:

Group I

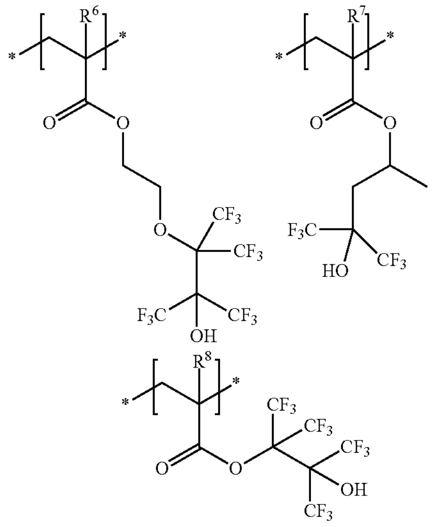

-continued

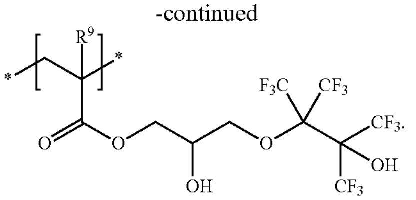

In Group I, $R^6$ to $R^9$ may each independently be hydrogen or a methyl group, and * is a linking point.

For example, the second structural unit may be represented by Chemical Formula 2-1 or Chemical Formula 2-2:

Chemical Formula 2-1

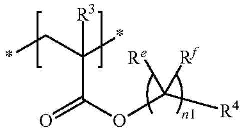

Chemical Formula 2-2

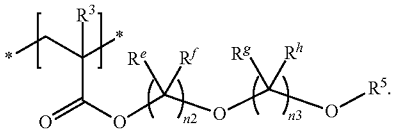

In Chemical Formula 2-1 and Chemical Formula 2-2, $R^3$ may be hydrogen or a substituted or unsubstituted C1 to C10 alkyl group, $R^e$, $R^f$, $R^g$, $R^h$, $R^4$, and $R^5$ may each independently be hydrogen, a hydroxy group, or a substituted or unsubstituted C1 to C10 alkyl group, n1 may be an integer of 5 to 10, n2 and n3 may each independently be an integer of 1 to 10, and

* is a linking point.

For example, n1 of Chemical Formula 2-1 may be an integer of 6 to 10, for example, an integer of 7 to 10.

For example, n2 and n3 of Chemical Formula 2-2 may each independently be an integer of 2 to 8, for example, an integer of 2 to 6.

For example, the second structural unit may be selected from Group II:

Group II

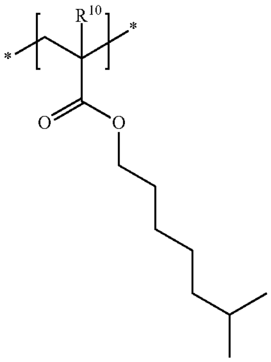

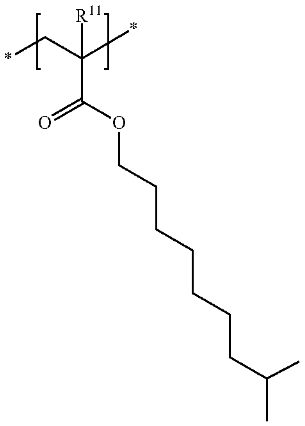

-continued

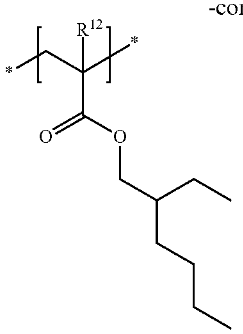

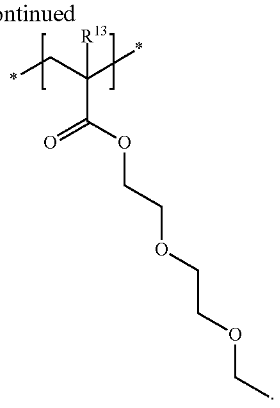

In Group II, $R^{10}$ to $R^{13}$ may each independently be hydrogen or a methyl group, and * is a linking point.

The acrylic copolymer may include the first structural unit and the second structural unit in a mole ratio of about 9:1 to about 5:5.

When the mole ratio of the structural units included in the acrylic copolymer is within the above range, the solubility of the acrylic copolymer in an organic solvent may be improved, and the composition may be substantially uniformly coated on the pattern.

For example, the acrylic copolymer may include the first structural unit and the second structural unit in a mole ratio of about 9:1 to about 6:4, for example, about 9:1 to about 7:3, and for example, about 9:1 or about 8:2 or about 7:3.

The acrylic copolymer may have a weight average molecular weight (Mw) of about 1,000 g/mol to about 50,000 g/mol. For example, it may have a weight average molecular weight of about 2,000 g/mol to about 30,000 g/mol, for example, about 3,000 g/mol to about 20,000 g/mol, or for example, about 4,000 g/mol to about 10,000 g/mol, but is not limited thereto. When the weight average molecular weight of the acrylic copolymer is within the above ranges, a carbon content (e.g., amount) and solubility in a solvent of the resist topcoat composition including the polymer may be enhanced and/or optimized.

In some embodiments, the acid compound included in the composition may be at least one selected from a sulfonic acid compound containing at least one fluorine, a sulfonimide compound containing at least one fluorine, and a carboxylic acid compound containing at least one fluorine.

For example, the acid compound included in the composition may be one type (class) of compound, and may be a sulfonic acid compound containing at least one fluorine, a sulfonimide compound containing at least one fluorine, or a carboxylic acid compound containing at least one fluorine.

For example, the acid compound included in the composition may include two types (classes) of compounds, and may be two selected from a sulfonic acid compound containing at least one fluorine, a sulfonimide compound containing at least one fluorine, and a carboxylic acid compound containing at least one fluorine.

For example, as a mixture including two types (classes) of acid compounds, a sulfonic acid compound containing at least one fluorine, and a sulfonimide compound containing at least one fluorine may be included in a weight ratio of about 1:0.1 to about 1:50. For example, the two acid compounds may be included in a weight ratio of about 1:0.3 to about 1:40, for example about 1:0.3 to about 1:35, or about 1:1 to about 1:30.

When a mixture including two types (classes) of acid compounds as described above is added, the defect portion of the resist may be selectively removed.

Accordingly, by utilizing the resist topcoat composition according to embodiments, a high-resolution pattern may be obtained with a high yield.

For example, the acid compound may be at least one compound represented by Chemical Formula 3 to Chemical Formula 6:

Chemical Formula 3

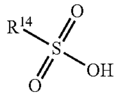

Chemical Formula 4

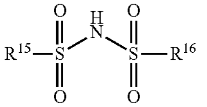

Chemical Formula 5

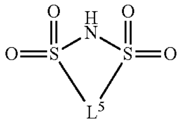

Chemical Formula 6

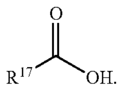

In Chemical Formula 3 to Chemical Formula 6, $R^{14}$ to $R^{17}$ may each independently be a fluorine, a C1 to C20 alkyl group substituted with at least one fluorine, a C2 to C20 alkenyl group substituted with at least one fluorine, a C2 to C20 alkynyl group substituted with at least one fluorine, a C3 to C20 cycloalkyl group substituted with at least one fluorine, a C3 to C20 cycloalkenyl group substituted with at least one fluorine, a C3 to C20 cycloalkynyl group substituted with at least one fluorine, a C6 to C20 aryl group substituted with at least one fluorine, or a C1 to C20 heteroaryl group substituted with at least one fluorine, and $L^5$ may be a C1 to C10 alkylene group substituted with at least one fluorine, a C3 to C20 cycloalkylene group substituted with at least one fluorine, a C6 to C20 arylene group substituted with at least one fluorine, or a C1 to C20 heteroarylene group substituted with at least one fluorine.

For example, $R^{14}$ to $R^{17}$ may each independently be a C1 to C10 alkyl group substituted with at least one fluorine, or a C6 to C20 aryl group substituted with at least one fluorine.

For example the acid compound may be selected from compounds of Group III:

Group III

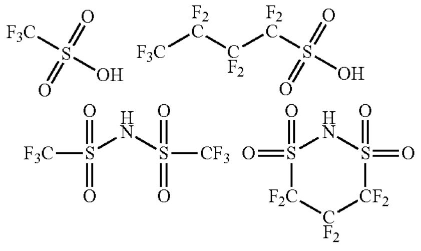

-continued

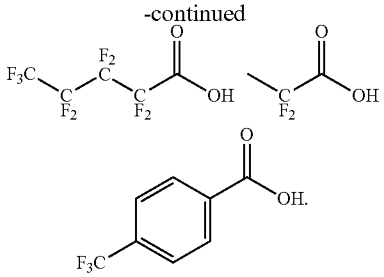

In some embodiments, the acrylic copolymer and the acid compound may be included in a weight ratio of about 3:1 to about 30:1, for example, about 5:1 to about 25:1, or about 5:1 to about 20:1.

By including the acrylic copolymer and the acid compound in the above weight ratio, the resist topcoat composition according to an embodiment may provide a resist topcoat that is easy to remove SLO defects.

A total content (e.g., amount) of the acrylic copolymer and the acid compound may be about 0.1 wt % to about 10 wt % based on the total weight of the resist topcoat composition. Within the above range, the resist topcoat may be easily removed.

In some embodiments, the resist topcoat composition may further include at least one other polymer selected from an epoxy-based resin, a novolac-based resin, a glycoluril-based resin, and a melamine-based resin, but is not limited thereto.

The resist topcoat composition may further include an additive including a surfactant, a thermal acid generator, a plasticizer, or any combination thereof.

The surfactant may be or include, for example, an alkylbenzene sulfonic acid salt, an alkylpyridinium salt, polyethylene glycol, a quaternary ammonium salt, and/or the like, but is not limited thereto.

The thermal acid generator may be, for example, an acid compound (such as p-toluene sulfonic acid, trifluoromethanesulfonic acid, pyridinium p-toluene sulfonic acid, salicylic acid, sulfosalicylic acid, citric acid, benzoic acid, hydroxybenzoic acid, naphthalene carboxylic acid, benzoin tosylate, 2-nitrobenzyl tosylate, and/or other organic sulfonic acid alkyl esters), but is not limited thereto.

The additive may be included in an amount of about 0.001 to about 40 parts by weight based on 100 parts by weight of the resist topcoat composition. Within the above range, solubility may be improved without changing the optical properties of the resist topcoat composition.

The solvent may be an ether-based solvent represented by Chemical Formula 7:

Chemical Formula 7

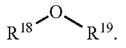

In Chemical Formula 7, $R^{18}$ and $R^{19}$ may each independently be a substituted or unsubstituted C3 to C20 alkyl group.

For example, the ether-based solvent may be selected from diisopropyl ether, dipropyl ether, diisoamyl ether, diamyl ether, dibutyl ether, diisobutyl ether, di-sec-butyl ether, dihexyl ether, bis(2-ethylhexyl) ether, didecyl ether, diundecyl ether, didodecyl ether, ditetradecyl ether, hexadecyl ether, butyl methyl ether, butyl ethyl ether, butyl propyl ether, tert-butyl methyl ether, tert-butyl ethyl ether, tert-butylpropyl ether, di-tert-butyl ether, cyclopentylmethyl ether, cyclohexylmethyl ether, cyclopentylethyl ether, cyclohexylethyl ether, cyclopentylpropyl ether, cyclopentyl-2-propyl ether, cyclohexylpropyl ether, cyclohexyl-2-propyl ether, cyclopentylbutyl ether, cyclopentyl-tert-butyl ether, cyclohexylbutyl ether, cyclohexyl-tert-butyl ether, 2-octanone, 4-heptanone, and combinations thereof.

The ether-based solvent may have sufficient solubility or dispersibility for the aforementioned composition.

Additional aspects of embodiments of the present disclosure provide for a photoresist pattern prepared utilizing the aforementioned resist topcoat composition. The resist topcoat may be in a cured film through a heat treatment process after coating the aforementioned resist topcoat composition on, for example, a photoresist pattern.

Hereinafter, a method of forming patterns utilizing the aforementioned resist topcoat composition is described with reference to the drawing.

A method of forming patterns according to an embodiment includes forming a photoresist pattern (e.g., a preliminary photoresist pattern) 102*a* on a substrate 100 (act 1), coating the aforementioned resist topcoat composition on the preliminary photoresist pattern 102*a*, drying and heating the substrate 100 on which the resist topcoat composition is coated to form a topcoat 30 (act 2), and spraying a rinse solution on the substrate coated with the topcoat to remove the topcoat (act 3).

The forming of the photoresist pattern on a substrate (act 1) may include coating a semiconductor resist composition on the substrate 100 by spin coating, slit coating, inkjet printing, etc., and then drying and heat treating the coated semiconductor photoresist composition to form a photoresist film 101, followed by selectively exposing and developing the photoresist film 101 to dissolve and remove the photoresist film corresponding to the exposed area to form a preliminary photoresist pattern 102*a*.

The forming of the preliminary photoresist pattern 102*a* may be performed by any suitable method in the art, and details thereof will not be provided.

In the preliminary photoresist pattern 102*a* formed in this way, defects such as the bridge 10 connecting adjacent patterns and the scum 20 remaining in the gap between the patterns may occur, which may cause later formation of SLO defects in the thin film pattern, and thereby cause a decrease of yield.

In the method of forming patterns according to an embodiment, in order to remove the bridge 10 and the scum 20 after the photoresist pattern is formed, the method may further include coating the aforementioned resist topcoat composition over the preliminary photoresist pattern 102*a*; drying and heating the substrate coated with the resist topcoat composition to form a topcoat 30 (act 2); and spraying a rinse solution on the substrate 100 coated with the topcoat 30 to remove the topcoat 30 (act 3).

The heating of the substrate 100 coated with the resist topcoat composition may be performed at a temperature of about 100° C. to about 500° C.

In the removing of the topcoat 30 by spraying a rinse solution, a solvent having low reactivity with respect to the photoresist and high solubility with respect to the topcoat may be advantageously utilized.

As such, in the photoresist pattern 102*b* formed after performing the coating of the topcoat 30 (act 2) and removing of the topcoat 30 (act 3), the bridge 10 and the scum 20 may be removed, compared with the photoresist pattern (e.g., the preliminary photoresist pattern) 102*a* formed before performing the processes (2) and (3), so that the patterning of the photoresist may be improved.

The thin film pattern 103 may be finally formed through a process (act 4) of etching the exposed thin film of the substrate 100 by applying the photoresist pattern 102*b* as an etching mask, and in the thin film pattern 103 formed in this way, SLO defects may be effectively removed without loss of the fine pattern.

The thin film may be etched, for example, by dry etching utilizing an etching gas, and the etching gas may be, for example, $CHF_3$, $CF_4$, $Cl_2$, $BCl_3$, or mixtures thereof.

In the exposure process described above, the thin film pattern formed using the photoresist pattern 102*b* that is formed by exposure process performed using the EUV light source may have a width corresponding to that of the photoresist pattern 102*b*. For example, the photoresist pattern 102*b* may have a width of about 5 nm to about 100 nm. For example, the thin film pattern 103 formed from the photoresist pattern 102*b* that is formed by the exposure process performed utilizing an EUV light source may have a width of about 5 nm to about 90 nm, about 5 nm to about 80 nm, about 5 nm to about 70 nm, about 5 nm to about 60 nm, about 5 nm to about 50 nm, about 5 nm to about 40 nm, about 5 nm to about 30 nm, about 5 nm to about 20 nm, similar to the photoresist pattern 102*b*, and in some embodiments, may for example be formed in a width of less than or equal to about 20 nm.

Hereinafter, the present disclosure will be described in more detail through examples relating to the synthesis of the aforementioned polymer and the preparation of a resist topcoat composition including the same. However, the present disclosure is not limited to or by the following examples.

SYNTHESIS EXAMPLES

Synthesis of Acrylic Polymer

Synthesis Example 1: Synthesis of Monomer 20 g (59.86 mmol) of hexafluoro-2,3-bis(trifluoromethyl)-2,3-butanediol(perfluoropinacol), 7.79 g (59.86 mmol) of 2-(hydroxyethyl)methacrylate, and 18.84 g (71.84 mmol) of triphenylphosphine ($Ph_3P$) were mixed in 110 mL of diethyl ether under a nitrogen atmosphere and then stirred. After stirring for 30 minutes, the mixture was cooled down to 0° C., and another mixture of 14.52 g (71.84 mmol) of diisopropylazodicarboxylate (DIAD) and 35 mL of diethyl ether was slowly added thereto over 2 hours. Subsequently, the obtained mixture was stirred at room temperature for 24 hours, and then concentrated. The concentrated mixture was dissolved in dichloromethane, and then treated through column chromatography by utilizing silica gel to separate a synthesized material. The separated material was distilled under a reduced pressure, obtaining 2-[3,3,3-trifluoro-2-hydroxy-1,1,2-tris(trifluoromethyl)propoxy]ethyl 2-methyl-2-propenoate represented by Chemical Formula 1a.

$^1$H-NMR (Acetone-d6): δ1.90 (3H, t), 4.36 (4H, m), 5.63 (1H, t), 6.09 (1H, t), 8.34 (1H, s)

$^{19}$F-NMR (Acetone-d6): δ−70.12 (6F, m), −65.38 (6F, m)

Chemical Formula 1a

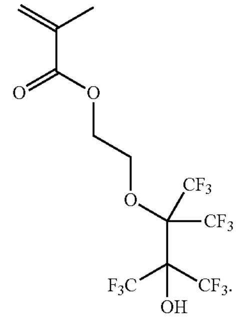

Synthesis Example 2: Preparation of Copolymer P1

The compound of Chemical Formula 1a (33.0 g, 67.2 mmol), and 6-methylheptyl methacrylate (3.33 g, 16.8 mmol, TCI Corporation) prepared in Synthesis Example 1 (e.g., as monomers) were put in a mole ratio of 8:2 in a 500 mL two-necked round flask under a nitrogen atmosphere, and dimethyl 2,2'-azobis(2-methylpropionate) (Wako Chemical, Inc., 2.5 g, 10.9 mmol) and diisoamyl ether (DIAE, 60 g) were additionally added thereto, and a condenser was connected thereto. After increasing the temperature to 110° C., the obtained mixture was reacted for 24 hours, and the reaction solution was cooled down to room temperature. The reaction solution was added dropwise with stirring into a 1 L wide-mouth bottle containing 225 g of heptane, producing a gum, and then, a supernatant was removed therefrom. After dissolving the remaining gum in 40 g of DIAE, 180 g of heptane was added thereto to form precipitates, and a supernatant was removed therefrom, which was repeated three times to remove monomers and oligomers.

Finally, 18.3 g (yield: 55%, weight average molecular weight: 5,000) of Copolymer P1 was obtained, the copolymer including structural units represented by Chemical Formula M-1-1 and Chemical Formula M-2-1:

Chemical Formula M-1-1

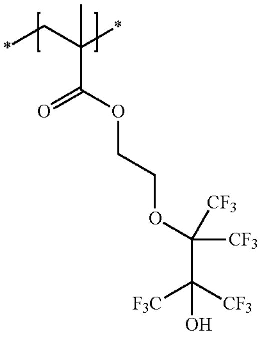

-continued

Chemical Formula M-2-1

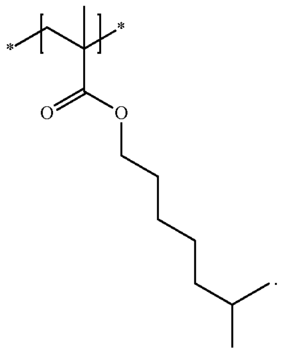

In Chemical Formula M-1-1 and Chemical Formula M-2-1, * is a linking point (e.g., to other units of the copolymer backbone).

Synthesis Example 3: Preparation of Copolymer P2

19.2 g (yield 60%, weight average molecular weight: 5,200) of Copolymer P2 including structural units represented by Chemical Formula M-1-1 and Chemical Formula M-2-2 was synthesized in substantially the same manner as in Synthesis Example 2, except that the compound of Chemical Formula 1a (33.0 g, 67.2 mmol) and 8-methylnonyl methacrylate (5.7 g, 25.2 mmol, TCI Corporation) prepared in Synthesis Example 1 (e.g., as monomers) were put in a mole ratio of 7:3 in a 500 mL two-necked round flask under a nitrogen atmosphere.

Chemical Formula M-1-1

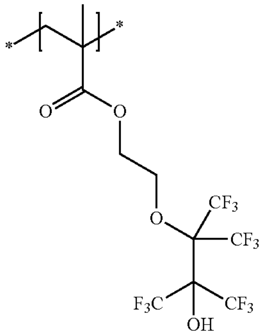

Chemical Formula M-2-2

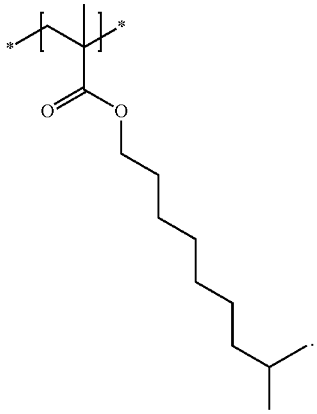

In Chemical Formula M-1-1 and Chemical Formula M-2-2, * is a linking point (e.g., to other units of the copolymer backbone).

Synthesis Example 4: Preparation of Copolymer P3

19.0 g (yield: 57%, weight average molecular weight: 4,500) of Copolymer P3 containing the structural unit represented by Chemical Formula M-1-1 and Chemical Formula M-2-3 was synthesized in substantially the same manner as in Synthesis Example 2, except that 2-ethylhexyl methacrylate (TCI) was utilized instead of 6-methylheptyl methacrylate as a monomer.

Chemical Formula M-1-1

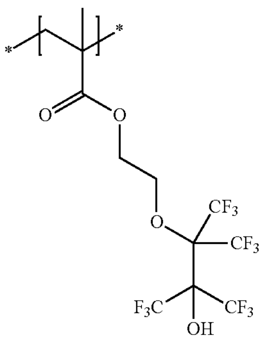

Chemical Formula M-2-3

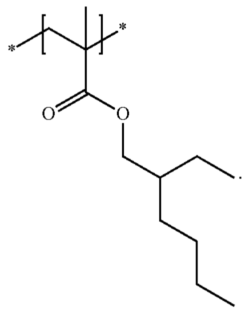

In Chemical Formula M-1-1 and Chemical Formula M-2-3, * is a linking point (e.g., to other units of the copolymer backbone).

Synthesis Example 5: Preparation of Copolymer P4

17.7 g (yield 50%, weight average molecular weight: 5,200) of Copolymer P4 including structural units represented by Chemical Formula M-1-1 and Chemical Formula M-2-4 was synthesized in substantially the same manner as in Synthesis Example 2, except that the compound of Chemical Formula 1a (33.75 g, 75.6 mmol) prepared in Synthesis Example 1 and 2-(2-ethoxyethoxy)ethyl methacrylate (1.7 g, 8.4) mmol, TCI Corporation) (e.g., as monomers) were put in a mole ratio of 9:1 in a 500 mL two-necked round flask under a nitrogen atmosphere.

Chemical Formula M-1-1

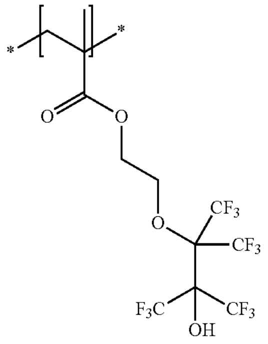

Chemical Formula M-2-4

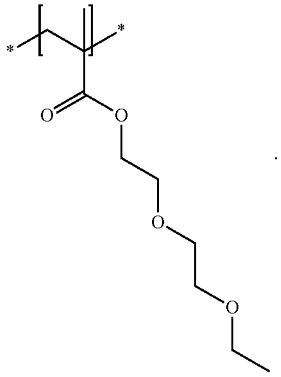

In Chemical Formula M-1-1 and Chemical Formula M-2-4, * is a linking point (e.g., to other units of the copolymer backbone).

Comparative Synthesis Example 1: Preparation of Copolymer P5

21.4 g (yield 63%, weight average molecular weight: 5,700) of Copolymer P5 including structural units represented by Chemical Formula M-1-1 and Chemical Formula M-3 was synthesized in substantially the same manner as in Synthesis Example 2, except that the compound of Chemical Formula 1a (33.0 g, 67.2 mmol) prepared in Synthesis Example 1 and 3-hydroxyadamantan-1-yl methacrylate (4.0 g, 16.8) mmol, TCI Corporation) (e.g., as monomers) were put in a mole ratio of 8:2 in a 500 mL two-necked round flask under a nitrogen atmosphere.

Chemical Formula M-1-1

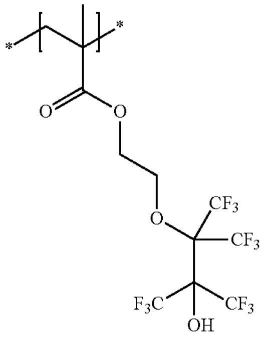

-continued

Chemical Formula M-3

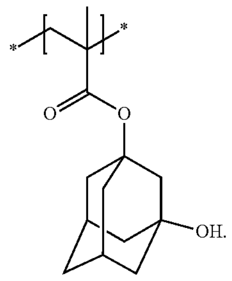

In Chemical Formula M-1-1 and Chemical Formula M-3, * is a linking point (e.g., to other units of the copolymer backbone).

Comparative Synthesis Example 2: Preparation of Copolymer P6

18.0 g (yield 56%, weight average molecular weight: 5,800) of Copolymer P6 including structural units represented by Chemical Formula M-1-1 and Chemical Formula M-3 was synthesized in substantially the same manner as in Synthesis Example 2, except that the compound of Chemical Formula 1a (26.3 g, 58.8 mmol), and 3-hydroxyadamantan-1-yl methacrylate (6.0 g, 25.2 mmol, TCI Corporation) (e.g., as monomers) were put in a mole ratio of 7:3 in a 500 mL two-necked round flask under a nitrogen atmosphere.

Preparation of Resist Topcoat Composition

Example 1

2 g (4.3 wt %) of Copolymer P1 prepared in Synthesis Example 2, 0.04 g (0.09 wt %) of trifluoromethylsulfonic acid, and 0.10 g (0.22 wt %) of bis(trifluoromethanesulfonyl)imide were dissolved in 44.4 g (95.4 wt %) of diisoamyl ether and stirred at room temperature (23° C.) for 24 hours to prepare a resist topcoat composition according to Example 1.

Examples 2 to 4 and Comparative Examples 1 and 2

Additional resist topcoat compositions were prepared in substantially the same manner as in Example 1, except that Copolymers P2 to P6 according to Synthesis Examples 3 to 5 and Comparative Synthesis Examples 1 and 2 were used in place of Copolymer P1.

Evaluation 1: Evaluation of Solubility 3 g samples of the copolymers of Synthesis Examples 2 to 5 and Comparative Synthesis Examples 1 and 2 were measured out, 7 g of a mixed solvent (DIAE:Heptane=6:4 w/w) was added thereto, allowed to stir for 24 hours, and then observed with naked eyes to check whether or not precipitates were produced. The results are shown in Table 1.

(No precipitation—Solubility O, with precipitation—Solubility X)

Evaluation 2: Evaluation of Non-Pattern Wafer (NPW) Strip

Each photoresist topcoat composition was spin-on coated on a silicon substrate coated with a photoresist and then, heat-treated on a hot plate at 110° C. for 1 minute, forming an about 50 nm-thick topcoat for a photoresist. Subsequently, the substrate coated with the topcoat was rinsed with a rinse solution (diisoamylether (DIAE)), heat-treated on a hot plate at 110° C. for 1 minute and then, measured with respect to a thickness change of the photoresist, which was utilized to calculate an NPW strip according to the following equation, and the results are shown in Table 1.

(NPW strip=PR thickness (nm) after forming and rinsing a photoresist topcoat−initial PR thickness (nm))

Evaluation 3: Evaluation of SLO Defects

On a 12 inch silicon substrate, a substrate composed of (a lower SiON film—a spin-on carbon film—a topcoat) were sequentially formed. On the SiON film, a 1:1 line/space photoresist pattern with a pitch of 36 nm was formed in an EUV lithography method. The photoresist pattern was transferred into the lower SiON film through dry etching utilizing plasma. Then, all defects including bridge defects between the line patterns were inspected with a defect analysis equipment utilizing a deep UV (DUV) laser. The detected defects were classified by utilizing SEM, providing the number of the detected defects per unit area (ea/$cm^2$).

Herein, when the number of SLO defects without utilizing the photoresist topcoat compositions was converted into 100, '○' was given to a case that the number of defects was less than or equal to 80%, and 'X' was given to a case that the number of defects was greater than 80%.

TABLE 1

| | Solubility | NPW strip | SLO Defects |
|---|---|---|---|
| Example 1 | ○ | −3.5 | ○ |
| Example 2 | ○ | −3.1 | ○ |
| Example 3 | ○ | −2.6 | ○ |
| Example 4 | ○ | −3.4 | ○ |
| Comparative Example 1 | X | — | — |
| Comparative Example 2 | X | — | — |

Referring to Table 1, when the resist topcoat compositions according to Examples 1 to 4 were applied, the solubility of the copolymer in the rinse solution is improved, and it can be expected that the topcoat will be easily removed, and also, the NPW strip (effective when −5.0 nm to −2.5 nm) and the defect improvement effect were exhibited.

On the other hand, in the case of the resist topcoat compositions according to Comparative Examples 1 and 2, the solubility of the copolymer in the rinse solution was not good or suitable, so it was impossible to evaluate whether the NPW strip and defects were improved.

Terms such as "substantially," "about," and "~" are used as terms of approximation and not as terms of degree, and are intended to account for the inherent deviations in measured or calculated values that would be recognized by those of ordinary skill in the art. They may be inclusive of the stated value and an acceptable range of deviation as determined by one of ordinary skill in the art, considering the limitations and error associated with measurement of that quantity. For example, "about" may refer to one or more standard deviations, or ±30%, 20%, 10%, 5% of the stated value.

Numerical ranges disclosed herein include and are intended to disclose all subsumed sub-ranges of the same numerical precision. For example, a range of "1.0 to 10.0" includes all subranges having a minimum value equal to or greater than 1.0 and a maximum value equal to or less than 10.0, such as, for example, 2.4 to 7.6. Applicant therefore reserves the right to amend this specification, including the claims, to expressly recite any sub-range subsumed within the ranges expressly recited herein.

Embodiments of the present disclosure have been described and illustrated, however, the present disclosure is not limited to embodiments as described, and may be variously modified and transformed without departing from the spirit and scope of the present disclosure, as set forth in the following claims and equivalents thereof.

DESCRIPTION OF SOME OF THE SYMBOLS

1: forming a photoresist pattern on a substrate
2: coating the aforementioned resist topcoat composition on the photoresist pattern and drying and heating the substrate on which the resist topcoat composition is coated to form a topcoat
3: spraying a rinse solution on the substrate coated with the topcoat to remove the topcoat
4: etching the exposed thin film by applying the photoresist pattern as an etching mask
10: bridge 20: scum
30: topcoat
100: substrate 101: photoresist film
102*a*: preliminary photoresist pattern formed before performing coating and removing the topcoat
102*b*: photoresist pattern formed after performing coating and removing the topcoat
103: thin film pattern

What is claimed is:

1. A resist topcoat composition, the composition comprising:

an acrylic copolymer comprising a first structural unit represented by Chemical Formula M-1, and a second structural unit represented by Chemical Formula 2-1 or Chemical Formula 2-2;

an acid compound; and a solvent:

Chemical Formula M-1

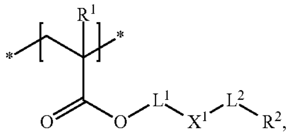

wherein, in Chemical Formula M-1, $R^1$ is hydrogen or a substituted or unsubstituted C1 to C10 alkyl group, $R^2$ is hydrogen, a fluorine, a hydroxy group, or a substituted or unsubstituted C1 to C20 alkyl group, $L^1$ and $L^2$ are each independently a single bond or a substituted or unsubstituted C1 to C10 alkylene group, $X^1$ is a single bond, —O—, —S—, —S(O)—, —$S(O)_2$—, —C(O)—, —(CO)O—, —O(CO), —O(CO)O—, or —NR'—, wherein R' is hydrogen, deuterium, or a C1 to C10 alkyl group, $R^2$, $L^1$, and $L^2$ together comprise a fluorine and a hydroxy group, and

* is a linking point; and

Chemical Formula 2-1

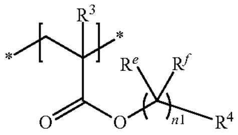

-continued

Chemical Formula 2-2

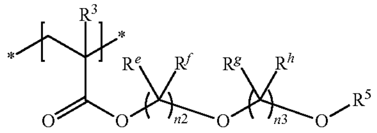

wherein in Chemical Formula 2-1 and Chemical Formula 2-2, $R^3$ is hydrogen or a substituted or unsubstituted C1 to C10 alkyl group, $R^e$, $R^f$, $R^g$, $R^h$, $R^4$, and $R^5$ are each independently hydrogen, a hydroxy group, or a substituted or unsubstituted C1 to C10 alkyl group, n1 is an integer of 5 to 10, n2 and n3 are each independently an integer of 1 to 10, and

* is a linking point.

2. The resist topcoat composition of claim 1, wherein the first structural unit is represented by Chemical Formula 1:

Chemical Formula 1

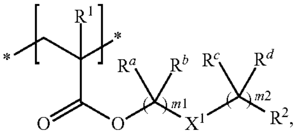

and wherein, in Chemical Formula 1, $R^1$ is hydrogen or a substituted or unsubstituted C1 to C10 alkyl group, $R^a$, $R^b$, $R^c$, $R^d$, and $R^2$ are each independently hydrogen, a fluorine, a hydroxy group, or a substituted or unsubstituted C1 to C20 alkyl group, m1 and m2 are each independently an integer from 1 to 10, $X^1$ is a single bond, —O—, —S—, —S(O)—, —$S(O)_2$—, —C(O)—, —(CO)O—, —O(CO), —O(CO)O—, or —NR'—, wherein R' is hydrogen, deuterium, or a C1 to C10 alkyl group, and $R^a$, $R^b$, $R^c$, $R^d$, and $R^2$ together comprise a fluorine and a hydroxy group.

3. The resist topcoat composition of claim 2, wherein $R^c$, $R^d$, and $R^2$ of Chemical Formula 1 together comprise a fluorine and a hydroxy group.

4. The resist topcoat composition of claim 2, wherein:

at least one of $R^c$ or $R^d$ of Chemical Formula 1 is a fluorine or a C1 to C10 alkyl group substituted with at least one fluorine, and $R^2$ is a hydroxy group or a C1 to C10 alkyl group substituted with at least one hydroxy group.

5. The resist topcoat composition of claim 2, wherein:

at least one of $R^c$ or $R^d$ in Chemical Formula 1 is a hydroxy group or a C1 to C10 alkyl group substituted with at least one hydroxy group, and $R^2$ is a fluorine or a C1 to C10 alkyl group substituted with at least one fluorine.

6. The resist topcoat composition of claim 2, wherein:

$R^c$ of Chemical Formula 1 is a hydroxy group or a C1 to C10 alkyl group substituted with at least one hydroxy group, $R^d$ is a fluorine or a C1 to C10 alkyl group substituted with at least one fluorine, and $R^2$ is a hydroxy group, a fluorine, or a C1 to C10 alkyl group substituted with at least one fluorine or at least one hydroxy group.

7. The resist topcoat composition of claim 2, wherein:

at least one of $R^c$ or $R^d$ of Chemical Formula 1 is a fluorine or a C1 to C10 alkyl group substituted with at least one fluorine, and $R^2$ is a hydroxy group, or a C1 to C10 alkyl group substituted with at least one hydroxy group and at least one fluorine.

8. The resist topcoat composition of claim 1, wherein the first structural unit is at least one selected from Group I:

Group I

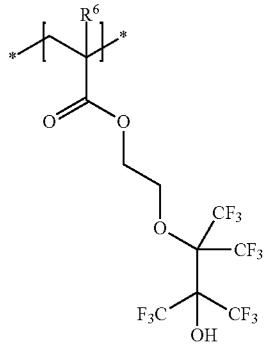

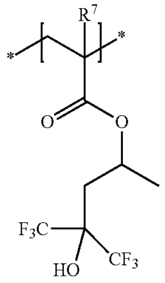

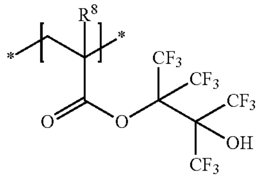

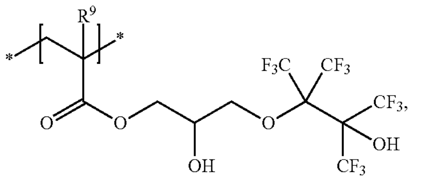

and wherein, in Group I, $R^6$ to $R^9$ are each independently hydrogen or a methyl group, and * is a linking point.

9. The resist topcoat composition of claim 1, wherein the second structural unit is at least one selected from Group II:

Group II

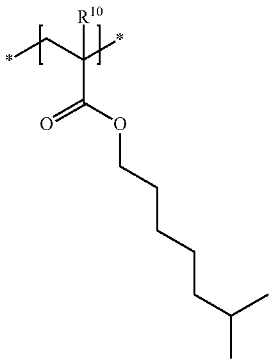

-continued

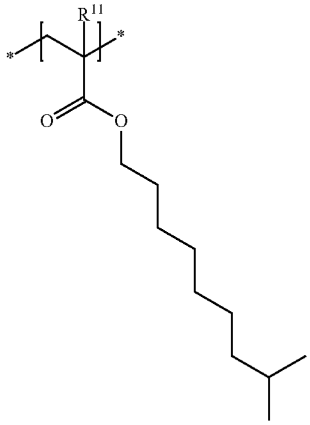

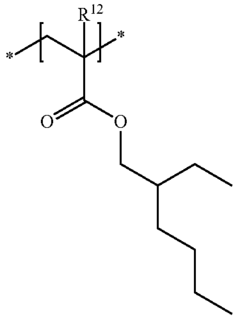

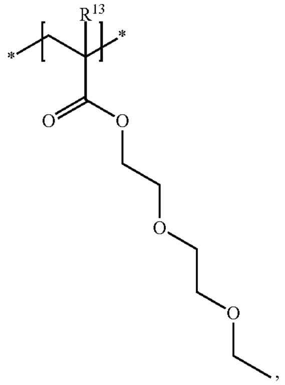

and wherein, in Group II, $R^{10}$ to $R^{13}$ are each independently hydrogen or a methyl group, and * is a linking point.

10. The resist topcoat composition of claim 1, wherein the acrylic copolymer comprises the first structural unit and the second structural unit in a mole ratio of about 9:1 to about 5:5.

11. The resist topcoat composition of claim 1, wherein a weight average molecular weight of the acrylic copolymer is about 1,000 g/mol to about 50,000 g/mol.

12. The resist topcoat composition of claim 1, wherein the acid compound is at least one selected from a sulfonic acid compound containing at least one fluorine, a sulfonimide compound containing at least one fluorine, and a carboxylic acid compound containing at least one fluorine.

13. The resist topcoat composition of claim 1, wherein the acid compound is represented by at least one of Chemical Formula 3 to Chemical Formula 6:

Chemical Formula 3

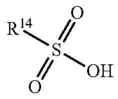

Chemical Formula 4

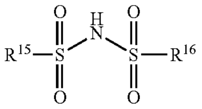

Chemical Formula 5

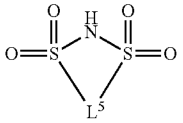

Chemical Formula 6

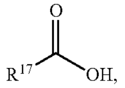

and wherein, in Chemical Formula 3 to Chemical Formula 6, $R^{14}$ to $R^{17}$ are each independently a fluorine, a C1 to C20 alkyl group substituted with at least one fluorine, a C2 to C20 alkenyl group substituted with at least one fluorine, a C2 to C20 alkynyl group substituted with at least one fluorine, a C3 to C20 cycloalkyl group substituted with at least one fluorine, a C3 to C20 cycloalkenyl group substituted with at least one fluorine, a C3 to C20 cycloalkynyl group substituted with at least one fluorine, a C6 to C20 aryl group substituted with at least one fluorine, or a C1 to C20 heteroaryl group substituted with at least one fluorine, and $L^5$ is a C1 to C10 alkylene group substituted with at least one fluorine, a C3 to C20 cycloalkylene group substituted with at least one fluorine, a C6 to C20 arylene group substituted with at least one fluorine, or a C1 to C20 heteroarylene group substituted with at least one fluorine.

14. The resist topcoat composition of claim 1, wherein the acid compound is selected from compounds of Group III:

Group III

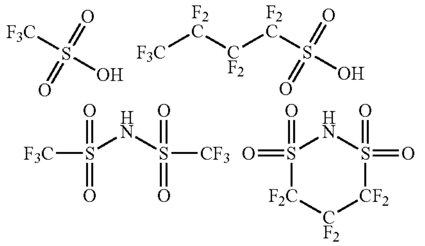

-continued

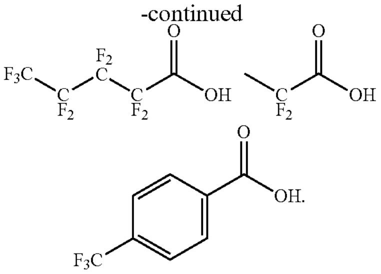

15. The resist topcoat composition of claim 1, wherein the acrylic copolymer and the acid compound are included in a weight ratio of about 3:1 to about 30:1.

16. The resist topcoat composition of claim 1, wherein a total content of the acrylic copolymer and the acid compound is about 0.1 wt % to about 10 wt % based on the total weight of the resist topcoat composition.

17. The resist topcoat composition of claim 1, wherein the solvent is an ether-based solvent represented by Chemical Formula 7:

Chemical Formula 7

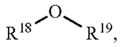

and wherein, in Chemical Formula 7, $R^{18}$ and $R^{19}$ are each independently a substituted or unsubstituted C3 to C20 alkyl group.

18. The resist topcoat composition of claim 17, wherein the ether-based solvent is at least one selected from diisopropyl ether, dipropyl ether, diisoamyl ether, diamyl ether, dibutyl ether, diisobutyl ether, di-sec-butyl ether, dihexyl ether, bis(2-ethylhexyl) ether, didecyl ether, diundecyl ether, didodecyl ether, ditetradecyl ether, hexadecyl ether, butyl methyl ether, butyl ethyl ether, butyl propyl ether, tert-butyl methyl ether, tert-butyl ethyl ether, tert-butylpropyl ether, di-tert-butyl ether, cyclopentylmethyl ether, cyclohexylmethyl ether, cyclopentylethyl ether, cyclohexylethyl ether, cyclopentylpropyl ether, cyclopentyl-2-propyl ether, cyclohexylpropyl ether, cyclohexyl-2-propyl ether, cyclopentylbutyl ether, cyclopentyl-tert-butyl ether, cyclohexylbutyl ether, cyclohexyl-tert-butyl ether, 2-octanone, 4-heptanone, and combinations thereof.

19. A method of forming patterns, the method comprising:

forming a photoresist pattern on a substrate, coating the resist topcoat composition of claim 1 on the photoresist pattern, drying and heating the substrate on which the resist topcoat composition is coated to form a topcoat, and spraying a rinse solution to remove the topcoat.

* * * * *